(12) United States Patent
Stahl et al.

(10) Patent No.: US 6,716,853 B2
(45) Date of Patent: Apr. 6, 2004

(54) CYCLIC N-SUBSTITUTED ALPHA-IMINO CARBOXYLIC ACIDS FOR SELECTIVE INHIBITION OF COLLOGENASE

(75) Inventors: Petra Stahl, Frankfurt (DE); Reinhard Kirsch, Braunschweig (DE); Sven Ruf, Flöersheim (DE); Volkmar Wehner, Sandberg (DE); Klaus-Ulrich Weithmann, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/374,569

(22) Filed: Feb. 26, 2003

(65) Prior Publication Data

US 2003/0199543 A1 Oct. 23, 2003

Related U.S. Application Data

(60) Provisional application No. 60/372,011, filed on Apr. 12, 2002.

(30) Foreign Application Priority Data

Mar. 2, 2002 (DE) .......................... 102 09 299

(51) Int. Cl.$^7$ ................ C07D 217/12; A61K 31/47
(52) U.S. Cl. .................. 514/303; 514/309; 546/118; 546/142
(58) Field of Search ................ 546/118, 142; 514/303, 309

(56) References Cited

U.S. PATENT DOCUMENTS 6,207,672 B1   3/2001   Thorwart

FOREIGN PATENT DOCUMENTS

| EP | 0 606 046 B1 | 10/1997 |
| EP | 0 861 236 B1 | 2/2002 |
| WO | WO 94/28889 | 12/1994 |
| WO | WO 96/27583 | 9/1996 |
| WO | WO 97/18194 | 5/1997 |

OTHER PUBLICATIONS

Klutchko Sylvester et al., 4,5,6,7–Tetrahydro–1H–imidazo [4,5–c]pyridine–6–carboxylic Acids, J. Heterocyclic Chem., 1991, vol. 28, pp 97–108.
Massova Irina et al., Matrix Metalloproteinases: Structures, Evolution, and Diversification, The FASEB Journal, 1998, vol. 12, pp 1075–1095.
Michaelides Michael R et al., Recent Advances in Matrix Metalloproteinase Inhibitors Research, Current Pharmaceutical Design, 1999, vol. 5, pp 787–819.
Ye Qi–Zhuang et al., Purification and Characterization of the Human Stromelysin Catalytic Domain Expressed in *Escherichia coli*, Biochemistry, 1992, vol. 31, pp 11231–11235.
Yip, Desmond et al., Matrix Metalloproteinase Inhibitors: Applications in Oncology, Investigational New Drugs, 1999, vol. 17, pp 387–399.

*Primary Examiner*—Zinna Northington Davis
(74) *Attorney, Agent, or Firm*—Julie Anne Knight; Paul R. Darkes

(57) ABSTRACT

The invention is related to compounds of formula I

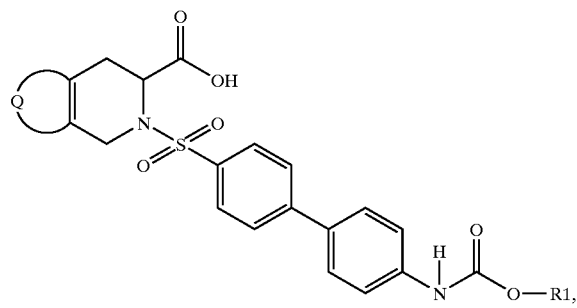

to pharmaceutical compositions comprising such compounds, to processes for the preparation of such compounds, and to methods of prevention and treatment of disorders, the progression of which involve an enhanced activity of matrix metalloproteinase 13, by administering to a patient in need thereof, a pharmaceutically effective amount of such compounds.

22 Claims, No Drawings

CYCLIC N-SUBSTITUTED ALPHA-IMINO CARBOXYLIC ACIDS FOR SELECTIVE INHIBITION OF COLLOGENASE

This application claims the benefit of U.S. Provisional Application No. 60/372,011, filed Apr. 12, 2002 and German Application No. 10209299.0 filed Mar. 2, 2002.

SUMMARY OF THE INVENTION

The invention relates to the use of cyclic N-substituted alpha-imino carboxylic acids of the formula I for selective inhibition of collagenase (MMP 13). The compounds of the formula I can therefore be employed for treating degenerative joint disorders.

BACKGROUND OF THE INVENTION

In disorders such as osteoarthritis and rheumatism there is destruction of the joint caused in particular by the proteolytic degradation of collagen by collagenases. Collagenases belong to the superfamily of metalloproteinases (MP) or matrix metallproteinases (MMP). The MMPs form a group of Zn-dependent enzymes which are involved in biological degradation of the extracellular matrix (D. Yip et al in Investigational New Drugs 17 (1999), 387–399 and Michaelides et al in Current Pharmaceutical Design 5 (1999) 787–819). These MMPs are able in particular to degrade fibrillary and non-fibrillary collagen, and proteoglycans, both of which represent important matrix constituents. MMPs are involved in processes of wound healing, of tumor invasion, of metastasis migration and in angiogenesis, multiple sclerosis, heart failure and atherosclerosis (Michaelides p. 788; see above). In particular, they play an important part in degradation of the joint matrix in arthrosis and arthritis, whether osteoarthrosis, osteoarthritis or rheumatoid arthritis.

A selected subgroup within the MMPs is formed, for example, by collagenases. Only collagenases are able to degrade native collagen which exercises an important supporting function in the matrix. This subgroup consists of interstitial collagenase MMP-1, of neutrophil collagenase MMP-8, and of MMP-13 which was identified only later. It was virtually impossible to detect MMP-13 in the body of healthy adult individuals; it is expressed only during the course of diseases, e.g. in cancer cells or ulcers. MMP-13 has also been detected in the joint matrix of arthrotic people and mammals, especially in clinically advanced arthrosis, while it does not occur in the joint tissue of healthy adults. Inhibition of MMP-13 by appropriate inhibitors is therefore particularly suitable for controlling said diseases.

A large number of different inhibitors of MMPs and of collagenases are known (EP 0 606 046; WO94/28889; WO 96/27583). It is also known that cyclic and heterocyclic N-substituted alpha-imino hydroxamic and carboxylic acids are inhibitors of metalloproteinases (EP 0 861 236).

After initial clinical studies on humans, it has now emerged that inhibitors of MMPs can cause side effects. The side effects which are mainly mentioned are musculoskeletal pain or arthralgias. It is, therefore, expected from the prior art that selective inhibitors will be able to reduce these side effects mentioned (Yip, page 387, see above).

A disadvantage of known inhibitors of MMPs is, therefore, frequently the lack of specificity of the inhibition for only one class of MMPs. Thus, most MMP inhibitors inhibit a plurality of MMPs simultaneously, because the MMPs have a catalytic domain of similar structure. Accordingly, the inhibitors act in an unwanted manner on many enzymes, even those with a vital function (Massova I, et al., The FASEB Journal (1998) 12, 1075–1095).

The application WO 97/18194 (EP 0 861 236) has already described cyclic and heterocyclic N-substituted alpha-imino hydroxamic and alpha-imino carboxylic acids which have a strong inhibitory effect on MMP-3 and MMP-8. The compounds disclosed by the description in the examples in WO 97/18194 also show a strong inhibitory effect on MMP-13.

In the effort to find effective compounds for the treatment of connective tissue disorders, it has now been found that the compounds employed according to the present invention are strong inhibitors of matrix metalloproteinase 13, while the compounds employed according to the invention are essentially ineffective for MMPs 3 and 8. These compounds employed according to the invention are thus more suitable in a much more targeted manner for the selective treatment of said diseases than the compounds disclosed and described in the examples in WO 97/18194, which inhibit other MMPs besides MMP-13. It is therefore to be expected that these selective inhibitors will show a considerable decrease in side effects on treatment of said disorders.

DETAILED DESCRIPTION OF THE INVENTION

The invention therefore relates compounds of the formula I

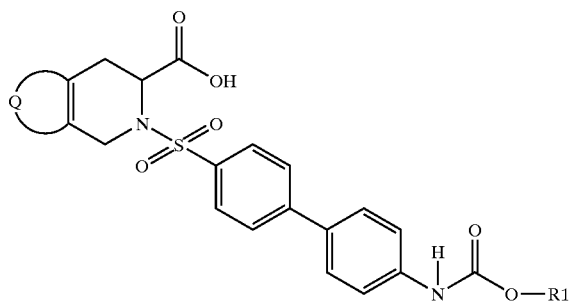

and/or all stereoisomeric forms of the compound of the formula I and/or mixtures of these forms in any ratio, and/or a physiologically tolerated salt of the compound of the formula I, wherein

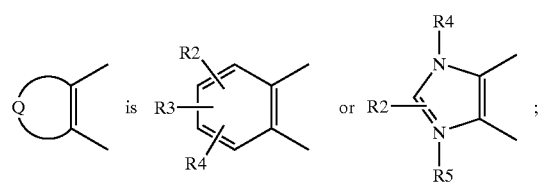

R1 is —$(C_1-C_{10})$-alkyl in which alkyl is linear or branched,
—$(C_2-C_{10})$-alkenyl in which alkenyl is linear or branched,
—$(C_2-C_{10})$-alkynyl in which alkynyl is linear or branched,
—$(C_1-C_4)$-alkylphenyl,
—$(C_1-C_4)$-alkyl-$(C_3-C_7)$-cycloalkyl,
—$(C_3-C_7)$-cycloalkyl, or
—$CH_2CF_3$; and
R2, R3, R4 and R5 are each, independently of one another, hydrogen, or —$(C_1-C_4)$-alkyl.

A preferred embodiment of the invention provides for compounds of formula I wherein and wherein R1, R2, R3, R4 and R5 are as defined above.

Another preferred embodiment of the invention provides for compounds of formula I wherein

[structure: Q ring is imidazole with R2, R4, R5]

and wherein R1, R2, R4 and R5 are as defined above.

Yet another preferred embodiment of the invention provides for compounds of formula I wherein

[structure: Q ring is benzene with R2, R3, R4 or imidazole with R2, R4, R5]

and wherein
R1 is —($C_2$–$C_6$)-alkyl in which alkyl is linear or branched, —$CH_2$-phenyl, or —$CH_2$-cyclopropyl; and
R2, R3, R4 and R5 are each, independently of one another, hydrogen or methyl.

Another preferred embodiment of the invention provides for compounds of formula I

[structure: Q ring is benzene with R2 or imidazole with R2, R4, R5]

wherein
R1 is —($C_1$–$C_{10}$)-alkyl in which alkyl is linear or branched,
—($C_2$–$C_{10}$)-alkenyl in which alkenyl is linear or branched,
—($C_2$–$C_{10}$)-alkynyl in which alkynyl is linear or branched,
—($C_1$–$C_4$)-alkylphenyl,
—($C_1$–$C_4$)-alkyl-($C_3$–$C_7$)-cycloalkyl,
—($C_3$–$C_7$)-cycloalkyl, or
—$CH_2CF_3$, and
R2, R4 and R5 are each, independently of one another, hydrogen, or —($C_1$–$C_4$)-alkyl.

The invention further relates to compounds of the formula II (II)

[structure of formula II]

wherein
R1 is —($C_2$–$C_6$)-alkyl in which alkyl is linear or branched, —$CH_2$-phenyl, or —$CH_2$-cyclopropyl; and
R2 is hydrogen or methyl.

A further aspect of the invention relates to compounds of the formula III (III)

[structure of formula III]

wherein
R1 is —($C_2$–$C_6$)-alkyl in which alkyl is linear or branched, —$CH_2$-phenyl, or —$CH_2$-cyclopropyl; and
R2 is hydrogen or methyl.

The invention also provides for pharmaceutical compositions comprising compounds of formula I and a pharmaceutically acceptable carrier.

The invention also provides for methods of preventing and treating disorders, the progression of which involves an enhanced activity of matrix metalloproteinase 13, by administering to a patient in need thereof, a pharmaceutically effective amount of a compound of formula I.

The invention further provides for methods of preventing and treating a degenerative joint disorder such as osteoarthroses, spondyloses, chondrolysis after joint trauma or prolonged joint immobilization after meniscus or patellar injuries or ligament tears, or connective tissue disorders such as collagenoses, periodontal disorders, wound healing disturbances, or chronic disorders of the locomotor system such as inflammatory, immunologically or metabolism-related acute or chronic arthritides, arthropathies, myalgias or disturbances of bone metabolism or an ulceration, atherosclerosis or stenosis, or inflammatory disorders, cancer, tumor metastasis, cachexia, anorexia or septic shock.

The term "($C_1$–$C_{10}$)-alkyl" means hydrocarbon radicals whose carbon chain is straight-chain or branched and contains 1 to 10 carbon atoms, for example methyl, ethyl, propyl, isopropyl, butyl, isobutyl, tertiary butyl, pentyl, isopentyl, neopentyl, hexyl, 2,3-dimethylbutyl, neohexyl, heptyl, octanyl, nonanyl, and decanyl.

The term "($C_2$–$C_{10}$)-alkenyl" means hydrocarbon radicals whose carbon chain is straight-chain or branched and contains 1 to 10 carbon atoms and, depending on the chain length, 1, 2 or 3 double bonds.

The term "$(C_2-C_{10})$-alkynyl" means hydrocarbon radicals whose carbon chain is straight-chain or branched and contains 1 to 10 carbon atoms and, depending on the chain length, 1, 2 or 3 triple bonds.

$(C_3-C_7)$-cycloalkyl radicals are, for example, compounds derived from 3- to 7-membered monocycles such as cyclopropyl, cyclobutyl, cyclopentyl, cyclohexyl and cycloheptyl.

"Patient" includes both human and other mammals.

"Effective amount" is meant to describe an amount of a compound or composition according to the present invention effective in producing the desired therapeutic effect.

The invention further relates to a process for preparing the compound of the formula I and/or a stereoisomeric form of the compound of the formula I and/or a physiologically tolerated salt of the compound of the formula I, which comprises a) reacting a compound of the formula IV

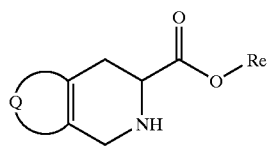
(IV)

in which

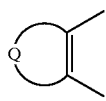

is as defined above for formula I, and Re is a hydrogen atom or an ester protective group, with a compound of the formula V,

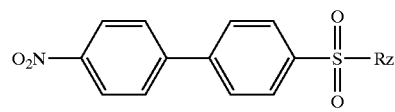
V in which Rz is chlorine, imidazolyl or OH, in the presence of a base to give a compound of the formula VI

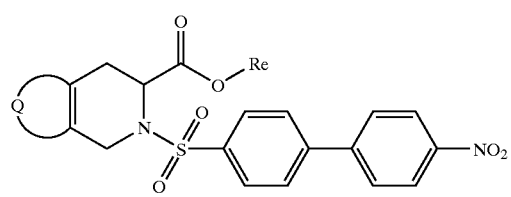
(VI)

in which

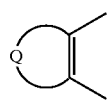

is as defined above for formula I, and Re is as defined above, and b) reducing a compound of the formula VI prepared as in a) with hydrogen and a metal catalyst to give an amine of the formula VII

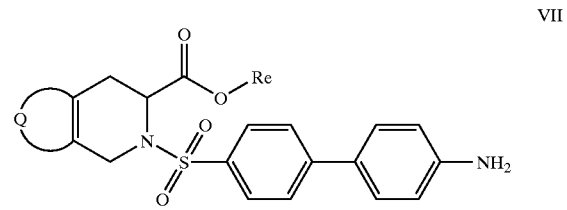
VII and subsequently reacting the compound of the formula VII with a compound of the formula VIII

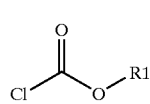
(VIII)

in which R1 is as defined in formula I,
in the presence of a basic compound such as triethylamine, trimethylamine or pyridine to give a compound of the formula IX,

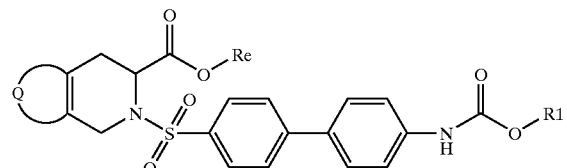
IX where

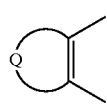

and R1 are as defined above for formula, and Re is as defined above; and,
where Re is an ester protecting group, followed by removal of the ester protecting group to give a compound of formula I; and c) fractionating a compound of the formula I which has been prepared as in step b) and which, because of its chemical structure, occurs in enantiomeric forms, into the pure enantiomers by salt formation with enantiopure acids or bases, chromatography on chiral stationary phases or derivatization using chiral enantiopure compounds such as amino acids, separation of the diastereomers obtained in this way, and elimination of the chiral auxiliary groups, or d) either isolating in free form the compound of the formula I prepared as in step b) or step c) or, in the case where acidic or basic groups are present, converting into a physiologically tolerated salt.

It is possible to employ as ester protective group Re the groups as protective groups for esters in Protective Groups in Organic Synthesis, T. H. Greene, P. G. M. Wuts, Wiley-Interscience, 1991. Preferred ester protective groups are, for example, methyl, ethyl, isopropyl, tert-butyl or benzyl.

The starting materials and reagents employed can either be prepared by known processes or be purchased. The spinacine ring system can be prepared for example as described by S. Klutchko et al. (J. Heterocyclic. Chem., 28, 97, (1991)).

The reactions take place for example as described in WO 97/18194. The reaction in process step a) takes place in the presence of a base such as KOH, NaOH, LiOH, N,O-bis (trimethylsilyl)acetamide (BSA), N-methylmorpholine (NMM), N-ethylmorpholine (NEM), triethylamine (TEA), diiusopropylethylamine (DIPEA), pyridine, collidine, imidazole or sodium carbonate in solvents such as tetrahydrofuran (THF), dimethylformamide (DMF), dimethylacetamide, dioxane, acetonitrile, toluene, chloroform or methylene chloride, or else in the presence of water.

The reaction in process step b) takes place for example using the metal catalysts Pd/C, $SnCl_2$ or Zn under standard conditions.

In process step c), the compound of the formula I is, if it occurs in diastereoisomeric or enantiomeric form and results as mixtures thereof in the chosen synthesis, separated into the pure stereoisomers, either by chromatography on an optionally chiral support material or, if the racemic compound of the formula I is able to form salts, by fractional crystallization of the diastereomeric salts formed with an optically active base or acid as auxiliary. Examples of suitable chiral stationary phases for separation of enantiomers by thin-layer or column chromatography are modified silica gel supports (called Pirkle phases) and high molecular weight carbohydrates such as triacetyl cellulose. For analytical purposes, methods of gas chromatography on chiral stationary phases can also be used after appropriate derivatization known to the skilled worker. To separate enantiomers of the racemic carboxylic acids, an optically active, usually commercially available, base such as (−)-nicotine, (+)- and (−)-phenylethylamine, quinine bases, L-lysine or L- and D-arginine are used to form the diastereomeric salts which differ in solubility, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I which contain a basic group such as an amino group with optically active acids such as (+)-camphor-10-sulfonic acid, D- and L-tartaric acid, D- and L-lactic acid and (+)- and (−)-mandelic acid into the pure enantiomers. Chiral compounds which contain alcohol or amine functions can also be converted with appropriately activated or optionally N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. It is then possible to make use of the chirality of the amino acid or alcohol residue introduced in enantiopure form for separating the isomers by carrying out a separation of the diastereomers which are now available by crystallization or chromatography on suitable stationary phases and then eliminating the included chiral moiety using suitable methods.

Acidic or basic products of the compound of the formula I may be in the form of their salts or in free form. Preference is given to pharmacologically acceptable salts, also termed physiologically tolerated salts, e.g. alkali metal or alkaline earth metal salts, and hydrochlorides, hydrobromides, sulfates, hemisulfates, all possible phosphates, and salts of amino acids, natural bases or carboxylic acids.

Preparation of physiologically tolerated salts from compounds of the formula I which are able to form salts, including the stereoisomeric forms thereof, in process step d) takes place in a manner known per se. The compounds of the formula I form stable alkali metal, alkaline earth metal or optionally substituted ammonium salts with basic reagents such as hydroxides, carbonates, bicarbonates, alcoholates, and ammonia or organic bases, for example trimethylamine or triethylamine, ethanolamine or triethanolamine or else basic amino acids, for example lysine, omithine or arginine. If the compounds of the formula I have basic groups, it is also possible to prepare stable acid addition salts with strong acids. Suitable for this purpose are both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid.

The invention also relates to pharmaceuticals which have an effective content of at least one compound of the formula I and/or of a physiologically tolerated salt of the compound of the formula I and/or an optionally stereoisomeric form of the compound of the formula I, together with a pharmaceutically suitable and physiologically tolerated carrier (which may also be termed a pharmaceutically acceptable carrier), additive and/or other active ingredients and excipients.

Because of the pharmacological properties, the compounds of the invention are suitable for the selective prophylaxis and therapy of all disorders in the progress of which an enhanced activity of metalloproteinase 13 is involved. These include degenerative joint disorders such as osteoarthroses, spondyloses, chondrolysis after joint trauma or prolonged joint immobilization after meniscus or patellar injuries or ligament tears. They also include connective tissue disorders such as collagenoses, periodontal disorders, wound-healing disturbances and chronic disorders of the locomotor system such as inflammatory, immunologically or metabolism-related acute and chronic arthritides, arthropathies, myalgias and disturbances of bone metabolism. The compounds of the formula I are also suitable for the treatment of ulceration, atherosclerosis and stenoses. The compounds of the formula I are furthermore suitable for the treatment of inflammations, cancers, tumor metastasis, cachexia, anorexia and septic shock. Said disorders can be treated with the compounds employed according to the invention considerably more specifically and with a smaller range of side effects because essentially only MMP-13 is inhibited.

Administration of the pharmaceuticals of the invention can take place by oral, inhalational, rectal or transdermal administration or by subcutaneous, intraarticular, intraperitoneal or intravenous injection. Oral administration is preferred.

The invention also relates to a process for producing a pharmaceutical which comprises converting at least one compound of the formula I into a suitable dosage form with a pharmaceutically suitable and physiologically tolerated carrier and, where appropriate, further suitable active ingredients, additives or excipients.

Examples of suitable solid or pharmaceutical preparations are granules, powders, coated tablets, tablets, (micro) capsules, suppositories, syrups, oral solutions, suspensions, emulsions, drops, injectable solutions, and products with protracted release of active ingredient, in the production of which conventional aids such as carriers, disintegrants, binders, coating agents, swelling agents, glidants or lubricants, flavorings, thickeners and solubilizers are used. Excipients which are often used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, each unit containing as active ingredient a particular dose of the compound of the invention, of the formula I. In the case of solid dosage units such as tablets, capsules, coated tablets or suppositories, this dose can be up to about 1,000 mg, but preferably about 50 to 300 mg, and in the case of solutions for injection in ampoule form up to about 300 mg, but preferably about 10 to 100 mg.

The daily doses indicated for the treatment of an adult patient weighing about 70 kg are from about 20 mg to 1000 mg of active ingredient, preferably about 100 mg to 500 mg, depending on the activity of the compound of the formula I. However, in some circumstances, higher or lower daily doses may also be appropriate. The daily dose may be administered both by administration once a day in the form of a single dosage unit or else a plurality of smaller dosage units, and by administration more than once a day of divided doses at defined intervals.

Final products are usually determined by mass spectroscopic methods (FAB-, ESI-MS), with the main peak being indicated in each case. Temperatures are stated in degrees Celsius, RT means room temperature, (22° C. to 26° C.). Abbreviations used are either explained or correspond to the usual conventions.

The invention is explained in detail below, but is by no means limited to, the following examples.

PREPARATION EXAMPLES

The compounds of Examples 1, 3, 4 and 5 in table 1 were prepared in an analogous manner to the procedures described in example 2.

Example 2

Stage 1:

Preparation of 2-(4'-Nitrobiphenyl-4-sulfonyl)-1,2,3,4-tetrahydro-isoquinoline-3-(R)-carboxylic Acid 44.2 g (250 mmol) of 1,2,3,4-tetrahydroisoquinoline-3-(R)-carboxylic acid were dissolved in 500 ml of 1N aqueous sodium hydroxide solution and, while stirring, 150 g (300 mmol) of 4'-nitrobiphenyl-4-sulfonyl chloride dissolved in 500 ml of tetrahydrofuran were added. During this, the reaction temperature was kept below 25° C., and the pH of the solution was adjusted to pH 10 by adding 1N NaOH. The reaction mixture was stirred at room temperature for 12 hours (h).

For workup, the reaction solution was filtered through a clarifying layer of Celite® and then the filtrate was concentrated to one half the original volume in a rotary evaporator under reduced pressure. The resulting solution was acidified to pH 2 to 3 by adding 20% strength aqueous citric acid solution, whereupon the reaction product precipitated as a colorless solid. The resulting solid was filtered off and dried in a vacuum oven at 40° C.

77.9 g (71% of theory, colorless solid) were obtained. Mass spectrum: ESI: [M+H$^+$]: m/z=439.4.

Stage 2:

Preparation of methyl 2-(4'-Nitrobiphenyl-4-sulfonyl)-1,2,3,4-tetrahydro-isoquinoline-3-(R)-carboxylate 77.5 g (177 mmol) of the carboxylic acid prepared in stage 1 were added in portions to a solution of 65 ml of thionyl chloride (885 mmol) in 800 ml of methanol at a temperature of −15° C. to −10° C. The mixture was then stirred at 25° C. for 1 hour and at 50° C. for 1 hour.

For workup, the reaction solution was concentrated under reduced pressure and stirred with 300 ml of dichloromethane and 300 ml of saturated aqueous NaHCO$_3$ solution. The organic phase was then washed with water until neutral and dried over Na$_2$SO$_4$, and the solvent was removed under reduced pressure. The crude product (80 g, brown oil) obtained in this way was purified by chromatography on silica gel (40 μ–63 μ) with n-heptane:ethyl acetate=2:1 as mobile phase.

27 g (34% of theory, colorless oil) were obtained. Mass spectrum: ESI: [M+H$^+$]: m/z=453.4.

Stage 3:

Preparation of methyl 2-(4'-aminobiphenyl-4-sulfonyl)-1,2,3,4-tetrahydro-isoquinolinyl-3-(R)-carboxylate 53 g (117 mmol) of the nitro compound prepared in stage 2 were dissolved in 1.5 l of a 1:1 mixture of tetrahydrofuran (THF) and methanol and, after addition of 1 g of Pd (10% on activated carbon), hydrogenated with H$_2$ in a hydrogenation apparatus until H$_2$ uptake ceased (hydrogen consumption 7.2 l).

For workup, the catalyst was filtered through a clarifying layer of Celite®, and the filtrate was concentrated in a rotary evaporator under reduced pressure. The oily residue was taken up in dichloromethane and dried over Na$_2$SO$_4$, and the solvent was removed under reduced pressure. The crude product obtained in this way was recrystallized from diethyl ether.

45.7 g (93% of theory, colorless solid) were obtained. Mass spectrum: ESI: [M+H$^+$]: m/z=423.4.

Stage 4:

Preparation of methyl 2-(4'-Isopropoxycarbonylaminobiphenyl-4-sulfonyl)-1,2,3,4-tetrahydroisoquinoline-3-(R)-carboxylate 16.9 g (40 mmol) of the compound of stage 3 were dissolved in 200 ml of absolute dichloromethane and, while stirring at −70° C. to −60° C., successively 4.9 ml of pyridine (60 mmol) and 44 ml (44 mmol) of isopropyl chloroformate were added. The mixture was then stirred at this temperature for 3 h. For workup, the reaction mixture was hydrolyzed at 0° C. by adding 10 ml of water. After removal of the organic phase it was washed until neutral and dried with Na$_2$SO$_4$, and the solvent was removed under reduced pressure in a rotary evaporator. The residue obtained in this way crystallized after addition of 100 ml of n-pentane in the form of salmon-colored crystals.

20.1 g (98%, salmon-colored crystals) were obtained. Mass spectrum: ESI: [M+H$^+$]: m/z=509.5.

Stage 5:

Preparation of 2-(4'-Isopropoxycarbonylaminobiphenyl-4-sulfonyl)-1,2,3,4-tetrahydroisocquinoline-3-(R)-carboxylic acid 20 g of the carboxylic ester (39.4 mmol) prepared in stage 4 were dissolved in 200 ml of THF and, at 25° C., 48 ml 1M aqueous LiOH solution were added. The reaction solution was stirred at 25° C. for 3 h.

The reaction mixture was then concentrated under reduced pressure, the residue was taken up in 750 ml of water and filtered through a clarifying layer of Celite® with addition of activated carbon, and the mother liquor was acidified with aqueous citric acid. The precipitated reaction product was filtered and purified by chromatography on silica gel (40 μ–63 μ) using dichlormethane:methanol in the ratio 9:1 as mobile phase.

14.1 g (72% of theory, colorless solid) were obtained. Mass spectrum: ESI: [M+H$^+$]: m/z=495.2.

Example 6

Stage 1:

5-(4'-Nitrobiphenyl-4-sulfonyl)-1-methyl-4,5,6,7-tetrahydro-1H-imidazo[4,5-c]pyridine-6-carboxylic Acid 2 g of 1-methylspinacine (9.19 mmol) were dissolved in 15 ml of water and, at 0° C., 3 equivalents of a 3N NaOH solution (9.19 ml) were added. After 10 minutes (min), a solution of 4'-nitrobiphenyl-4-sulfonyl chloride (2.74 g, 9.19 mmol) in acetonitrile was slowly added dropwise and, after room temperature was reached, the mixture was stirred for a further 12 h. The crude product was purified by chromatography.

1.9 g (47% of theory, colorless solid) were obtained. Mass spectrum: ESI: [M+H$^+$]: m/z=443.

Stage 2:

5-(4'-Aminobiphenyl-4-sulfonyl)-1-methyl-4,5,6,7-tetrahydro-1H-imidazo[4,5-c]pyridine-6-carboxylic Acid 1 g (2.3 mmol) of 5-(4'-nitrobiphenyl-4-sulfonyl)-1-methyl-4,5,6,7-tetrahydro-1H-imidazo[4,5-c]pyridine-6-carboxylic acid was dissolved in 15 ml of dimethylformamide (DMF) and, after addition of 0.1 g of hydrogenation catalyst (10% Pd on activated carbon), quantitatively hydrogenated within 2 h. After removal of the solvent, the crude product was purified by chromatography.

0.74 g (78% of theory, colorless solid) were obtained. Mass spectrum: ESI: [M+H$^+$]: m/z=413.

Stage 3:

5-(4'-Alkoxycarbonylaminobiphenyl-4-sulfonyl)-1-methyl-4,5,6,7-tetrahydro-1H-imidazo[4,5-c]pyridine-6-carboxylic Acids 500 mg (1.2 mmol) of 5-(4'-aminobiphenyl-4-sulfonyl)-1-methyl-4,5,6,7-tetrahydro-1H-imidazo[4,5-c]pyridine-6-carboxylic acid were dissolved in 3 ml of DMF and, after cooling to 0° C. in an ice bath, 2.4 mmol of pyridine were added. After stirring at 0° C. for 15 min, 1.8 mmol of isopropyl chloroformate were added. The reaction solution was then stirred at room temperature for 2 h. The crude product was purified by chromatographic methods.

0.38 g (64% of theory, colorless solid) was obtained. Mass spectrum: ESI: [M+H$^+$]: m/z=499.

Compounds 7 to 10 in table 1 were prepared in an analogous manner to the procedures described in example 6.

TABLE 1

| Example | Structure | MS (ESI+) |
|---|---|---|
| 1 | 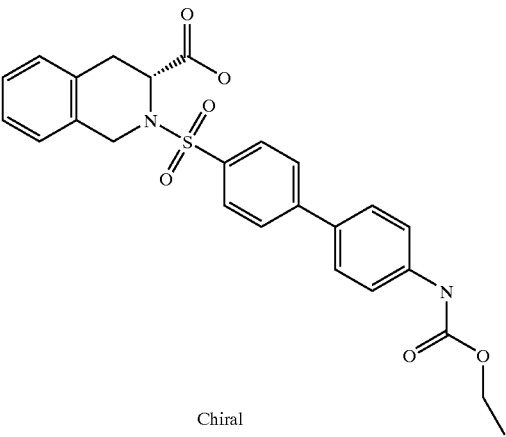 Chiral | 481 |
| 2 | 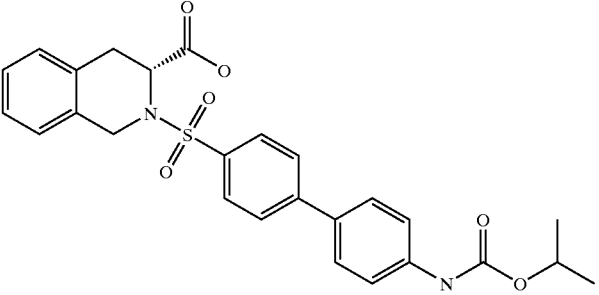 Chiral | 495 |

TABLE 1-continued
| Example | Structure | MS (ESI+) |
|---------|-----------|-----------|
| 3 | 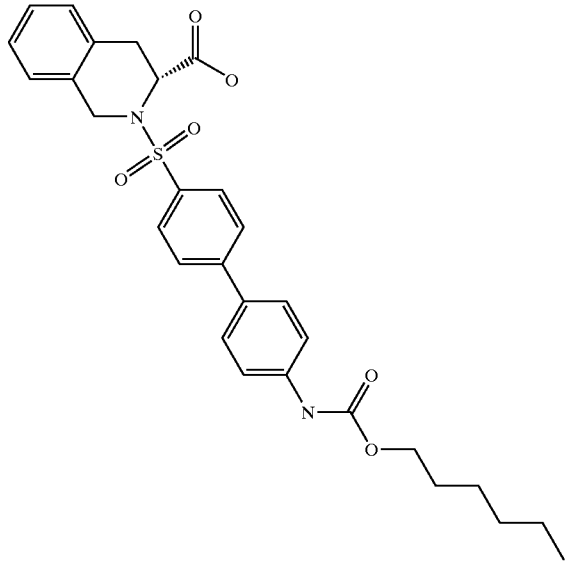 | 537 |
| 4 | 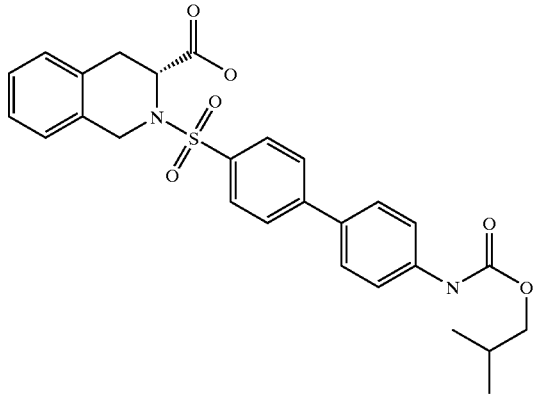 | 509 |
| 5 | 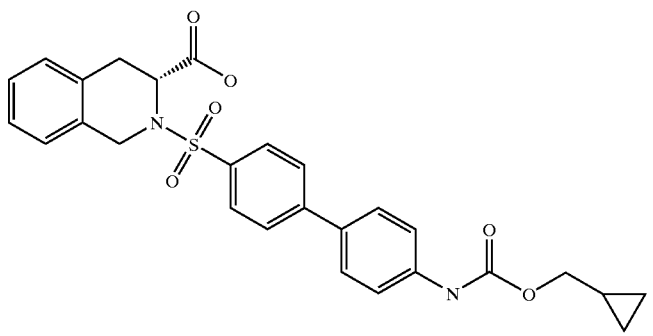 | 507 |

TABLE 1-continued

| Example | Structure | MS (ESI+) |
|---|---|---|
| 6 | 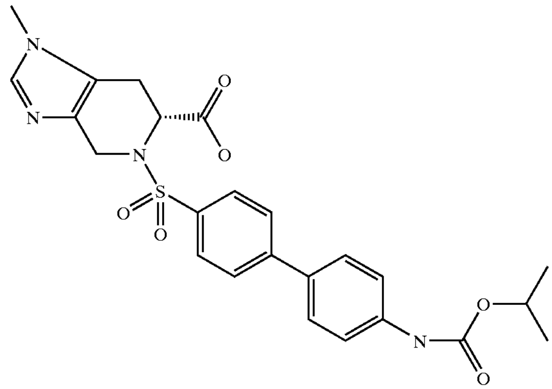 | 499 |
| 7 | 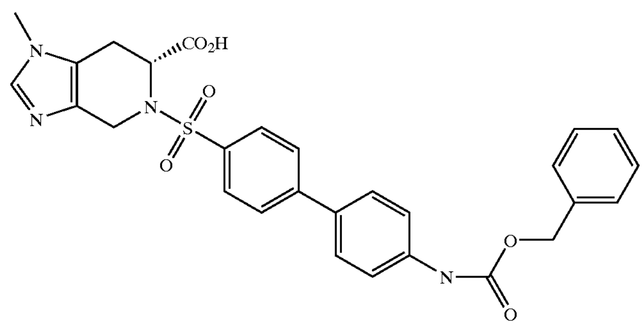 | 547 |
| 8 | 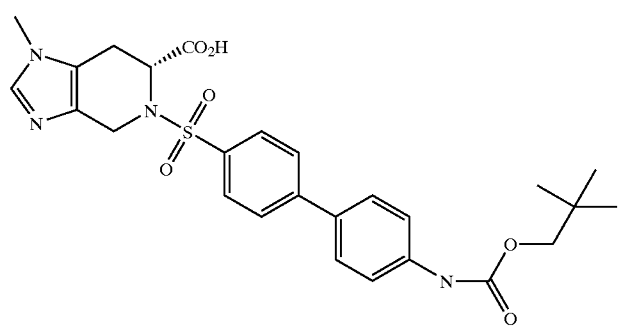 | 527 |
| 9 | 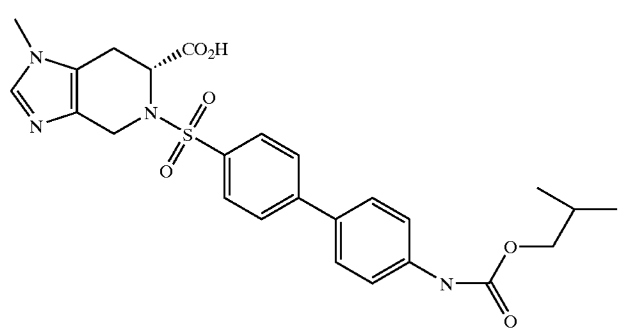 | 513 |

TABLE 1-continued

| Example | Structure | MS (ESI+) |
|---|---|---|
| 10 | 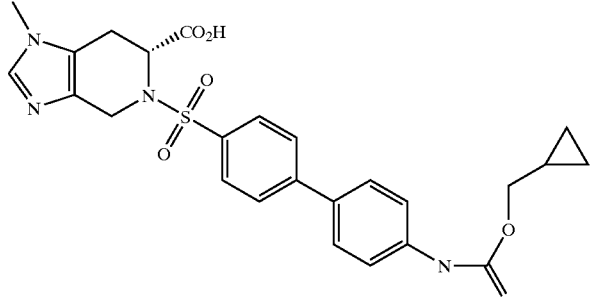 | 511 |

PHARMACOLOGICAL EXAMPLES

Preparation and determination of the enzymatic activity of the catalytic domain of human stromelysin (MMP 3) and neutrophil collagenase (MMP8).

The two enzymes—stromelysin (MMP-3) and neutrophil collagenase (MMP-8)—were prepared as described by Ye et al. (Biochemistry; 31 (1992) pages 11231–11235). To measure the enzymic activity or the enzyme inhibitory effect, 70 μl of buffer solution and 10 μl of enzyme solution are incubated at physiological pH with 10 μl of a 10% strength (v/v) aqueous dimethyl sulfoxide solution which optionally contains the enzyme inhibitor for 15 minutes. After addition of 10 μl of a 10% strength (v/v) aqueous dimethyl sulfoxide solution which contains 1 mmol/l of the substrate, the enzymic reaction is followed by fluorescence spectroscopy (328 nm (ex)/393 nm(em)).

The enzymic activity is represented as increase in extinction/minute. The $IC_{50}$ values listed in table 2 are measured as the inhibitor concentrations leading in each case to 50% inhibition of the enzyme.

The buffer solution contains 0.05% Brij (Sigma, Deisenhofen, Germany) and 0.1 mol/l Tris/HCl, 0.1 mol/l NaCl, 0.01 mol/l CaCl$_2$ and 0.1 mol/l piperazine-N,N'-bis [2-ethanesulfonic acid] (pH=7.5).

The enzyme solution contains 5 μg/ml of one of the enzyme domains prepared as described by Ye et al. The substrate solution contains 1 mmol/l of the fluorogenic substrate (7-methoxycoumarin-4-yl)acetyl-Pro-Leu-Gly-Leu-3-(2,4-dinitrophenyl)-L-2,3-diaminopropionyl-Ala-Arg-NH$_2$ (Bachem, Heidelberg, Germany).

Determination of the enzymatic activity of the catalytic domain of human collagenase 3 (MMP-13).

This protein is obtained as inactive proenzyme from INVITEK, Berlin (catalog No. 30 100 803). Activation of the proenzyme:

2 parts by volume of proenzyme are incubated with 1 part by volume of APMA solution at 37° C. for 1.5 hours. The APMA solution is prepared from a 10 mmol/L p-aminophenylmercuric acetate solution in 0.1 mmol/L NaOH by dilution with 3 parts by volume of Tris/HCl buffer pH7.5 (see below). The pH is adjusted to between 7.0 and 7.5 by adding 1 mmol/L HCl. After activation of the enzyme it is diluted with the Tris/HCl buffer to a concentration of 1.67 μg/mL.

To measure the enzymic activity, 10 μL of enzyme solution are incubated with 10 μL of a 3% strength (v/v) buffered dimethyl sulfoxide solution (reaction 1) for 15 minutes. To measure the enzyme inhibitory activity, 10 μL of enzyme solution are incubated with 10 μL of a 3% strength (v/v) buffered dimethyl sulfoxide solution which contains the enzyme inhibitor (reaction 2).

The enzymic reaction both in reaction 1 and in reaction 2 is followed, after addition of 10 μL of a 3% strength (v/v) aqueous dimethyl sulfoxide solution which contains 0.75 mmol/L of the substrate, by fluorescence spectroscopy (328 nm (extinction)/393 nm(emission)).

The enzymic activity is represented as increase in extinction/minute.

The inhibitory effect is calculated as percentage inhibition by the following formula:

% inhibition=100−[(increase in extinction/minute in reaction 2)/(increase in extinction/minute in reaction 1)×100].

The $IC_{50}$, i.e. the inhibitor concentration necessary for 50% inhibition of enzymic activity, is found by plotting a graph of the percentage inhibitions at various inhibitor concentrations.

The buffer solution contains 0.05% Brij (Sigma, Deisenhofen, Germany) and 0.1 mol/L Tris/HCl, 0.1 mol/L NaCl, 0.01 mol/L CaCl$_2$ (pH=7.5).

The enzyme solution contains 1.67 μg/mL of the enzyme domain.

The substrate solution contains 0.75 mmol/L of the fluorogenic substrate (7-methoxycoumarin-4-yl)acetyl-Pro-Leu-Gly-Leu-3-(2,4-dinitrophenyl)-L-2,3-diaminopropionyl-Ala-Arg-NH$_2$ (Bachem, Heidelberg, Germany).

Table 2 below shows the results.

TABLE 2

| Example No. | MMP 3 $IC_{50}$ (nM) | MMP 8 $IC_{50}$ (nM) | MMP 13 $IC_{50}$ (nM) |
|---|---|---|---|
| 1 | 3000 | 2300 | 40 |
| 2 | 3000 | 6000 | 30 |
| 3 | >10000 | 2000 | 70 |
| 4 | 2000 | 3000 | 20 |
| 5 | 3000 | 4000 | 20 |
| 6 | 10000 | 4000 | 80 |
| 7 | >10000 | 1000 | 60 |
| 8 | >10000 | 5000 | 70 |
| 9 | 10000 | 200 | 60 |
| 10 | >10000 | 700 | 20 |

COMPARATIVE EXAMPLES

The following compounds specified in table 3 were prepared as described in WO 97/18194.

TABLE 3

| Example No. | Structure | MMP 13[1] (nM) | MMP 3[2] (nM) | MMP 8[3] (nM) |
|---|---|---|---|---|
| 34 | 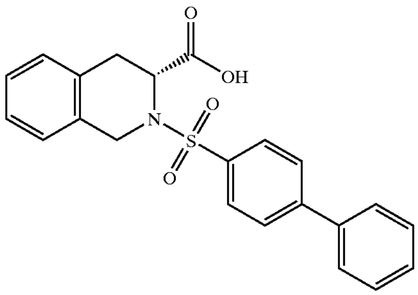 | 50 | 500 | 10 |
| 35 | 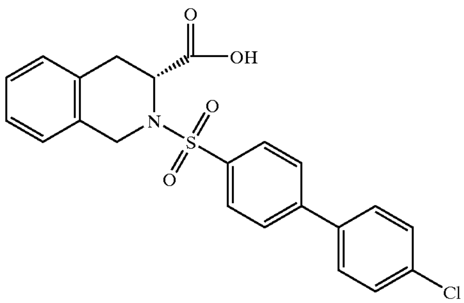 | 30 | 100 | 5 |
| 39 | 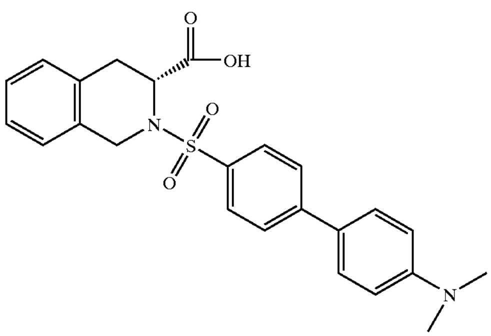 | 2.9 | 100 | 1 |

[1] Determination took place as described above
[2] and [3] The data were taken from WO 97/18194

Table 3 shows that structurally similar compounds from the prior art show no selectivity in inhibition only of MMP 13.

What is claimed is:

1. A compound of formula I

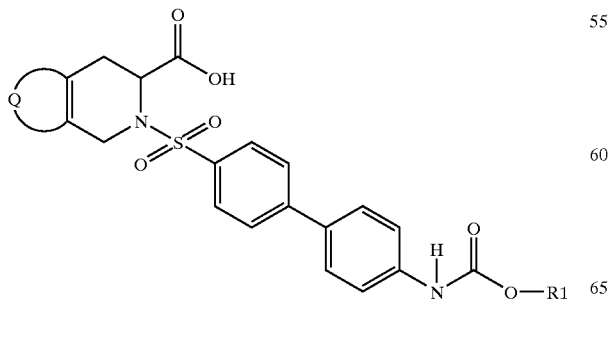

(I)

wherein

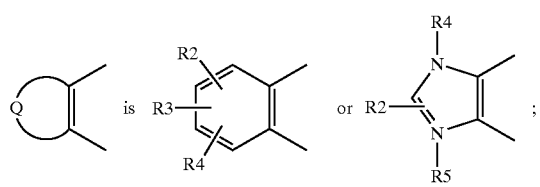

R1 is —($C_1$–$C_{10}$)-alkyl in which alkyl is linear or branched,
—($C_2$–$C_{10}$)-alkenyl in which alkenyl is linear or branched,
—($C_2$–$C_{10}$)-alkynyl in which alkynyl is linear or branched,
—($C_1$–$C_4$)-alkylphenyl,
—($C_1$–$C_4$)-alkyl-($C_3$–$C_7$)-cycloalkyl,
—($C_3$–$C_7$)-cycloalkyl, or
—$CH_2CF_3$; and R2, R3, R4 and R5 are each, independently of one another, hydrogen, or —(C$_1$–C$_4$)-alkyl; or a physiologically tolerated salt thereof.

2. A compound according to claim 1 wherein

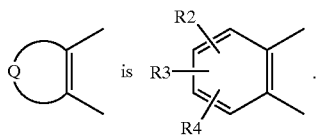

3. A compound according to claim 1 wherein

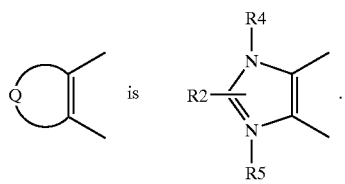

4. A compound according to claim 1 wherein

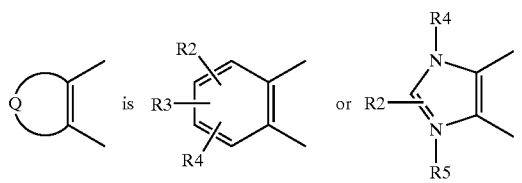

R1 is —(C$_2$–C$_6$)-alkyl in which alkyl is linear or branched, —CH$_2$-phenyl, or —CH$_2$-cyclopropyl; and R2, R3, R4 and R5 are each, independently of one another, hydrogen or methyl.

5. A compound according to claim 1 wherein

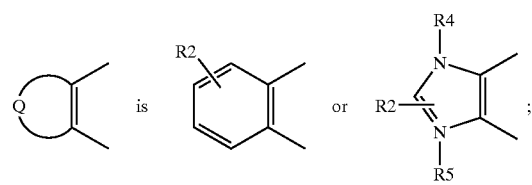

R1 is —(C$_1$–C$_{10}$)-alkyl in which alkyl is linear or branched,

—(C$_2$–C$_{10}$)-alkenyl in which alkenyl is linear or branched,

—(C$_2$–C$_{10}$)-alkynyl in which alkynyl is linear or branched,

—(C$_1$–C$_4$)-alkylphenyl,

—(C$_1$–C$_4$)-alkyl-(C$_3$–C$_7$)-cycloalkyl,

—(C$_3$–C$_7$)-cycloalkyl, or

—CH$_2$CF$_3$, and

R2, R4 and R5 are each, independently of one another, hydrogen, or —(C$_1$–C$_4$)-alkyl.

6. A compound according to claim 1 of formula II

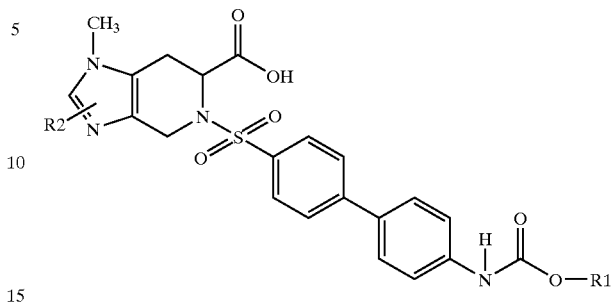

wherein

R1 is —(C$_2$–C$_6$)-alkyl in which alkyl is linear or branched, —CH$_2$-phenyl, or —CH$_2$-cyclopropyl; and R2 is hydrogen or methyl; or a physiologically tolerated salt thereof.

7. A compound according to claim 1 of formula III

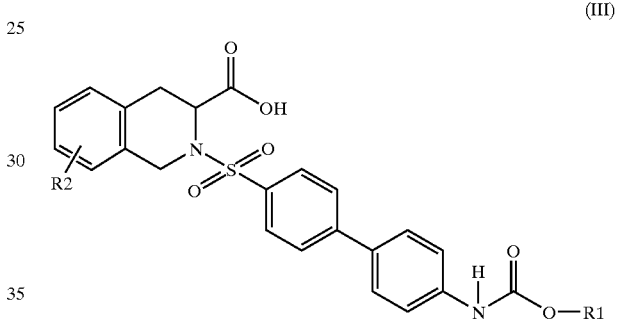

wherein

R1 is —(C$_2$–C$_6$)-alkyl in which alkyl is linear or branched, —CH$_2$-phenyl, or —CH$_2$-cyclopropyl; and R2 is hydrogen or methyl; or a physiologically tolerated salt thereof.

8. A pharmaceutical composition comprising a compound according to claim 1 and a pharmaceutically acceptable carrier.

9. A method of preventing or treating a disorder, the progression of which involves an enhanced activity of matrix metalloproteinase 13, by administering to a patient in need thereof, a pharmaceutically effective amount of a compound according to claim 1.

10. A method according to claim 9 wherein the disorder is a degenerative joint disorder.

11. A method according to claim 10 wherein the degenerative joint disorder is osteoarthrosis, spondylosis, or chondrolysis after joint trauma or prolonged joint immobilization after meniscus or patellar injuries or ligament tears.

12. A method according to claim 9 wherein the disorder is a connective tissue disorder.

13. A method according to claim 12 wherein the connective tissue disorder is collagenosis, a periodontal disorder, or a wound healing disturbance.

14. A method according to claim 9 wherein the disorder is a chronic disorder of the locomotor system.

15. A method according to claim 14 wherein the chronic disorder of the locomotor system is inflammatory, immunologically or metabolism-related acute or chronic arthritis, arthropathy, or myalgia.

16. A method according to claim 9 wherein the disorder is a disturbance of bone metabolism or an ulceration.

17. A method according to claim 9 wherein the disorder is atherosclerosis or stenosis.

18. A method according to claim 9 wherein the disorder is an inflammatory disorder.

19. A method according to claim 9 wherein the disorder is cancer or tumor metastasis.

20. A method according to claim 9 wherein the diorder is cachexia or anorexia.

21. A method according to claim 9 wherein the disorder is septic shock.

22. A process for preparing a compound according to claim 1 comprising a) reacting a compound of the formula IV

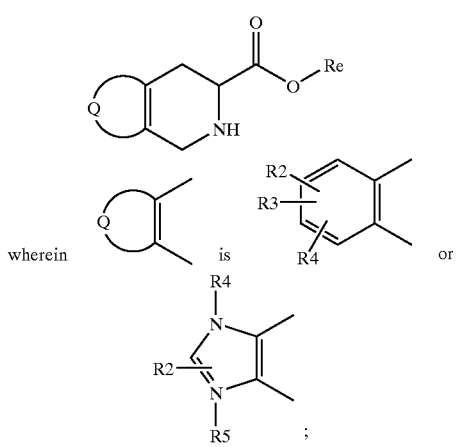

wherein $\underset{Q}{\bigcirc}\!\!\!=$ is 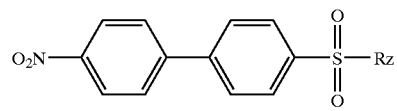 or 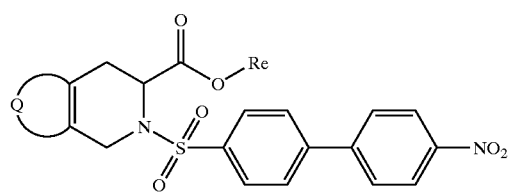 ;

R2, R3, R4 and R5 are each, independently of one another, hydrogen, or —($C_1$–$C_4$)-alkyl; and Re is a hydrogen atom or an ester protective group, with a compound of the formula V,

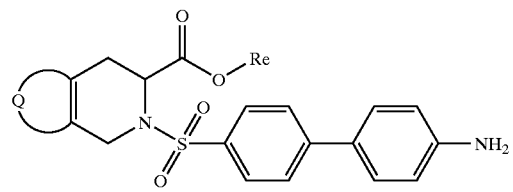

in which Rz is chlorine, imidazolyl or OH,
in the presence of a base to give a compound of the formula VI

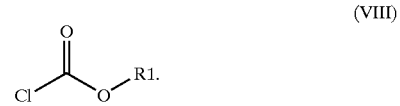

b) reducing a compound of the formula VI prepared as in a) with hydrogen and a metal catalyst to give an amine of the formula VII

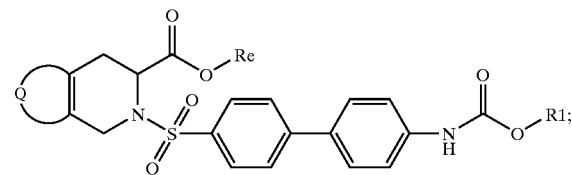

and subsequently reacting the compound of the formula VII with a compound of the formula VIII (VIII)

$$\underset{Cl}{\overset{O}{\|}}\!\!\!\!\!\!\underset{}{\text{—}}\!\!\!\!\!\!\overset{}{\text{O}}\!\!\!\!\!\!\text{—R1.}$$

wherein is R1 is —($C_1$–$C_{10}$)-alkyl in which alkyl is linear or branched,
—($C_2$–$C_{10}$)-alkenyl in which alkenyl is linear or branched,
—($C_2$–$C_{10}$)-alkynyl in which alkynyl is linear or branched,
—($C_1$–$C_4$)-alkylphenyl,
—($C_1$–$C_4$)-alkyl-($C_3$–$C_7$)-cycloalkyl,
—($C_3$–$C_7$)-cycloalkyl, or
—$CH_2CF_3$,
in the presence of a basic compound such as triethylamine, trimethylamine or pyridine to give a compound of the formula IX, and,
where Re is an ester protecting group, followed by removal of the ester protecting group to give a compound of formula I; and c) fractionating a compound of the formula I which has been prepared as in step b) and which, because of its chemical structure, occurs in enantiomeric forms, into the pure enantiomers by salt formation with enantiopure acids or bases, chromatography on chiral stationary phases or derivatization using chiral enantiopure compounds such as amino acids, separation of the diastereomers obtained in this way, and elimination of the chiral auxiliary groups, or d) either isolating in free form the compound of the formula I prepared as in step b) or step c) or, in the case where acidic or basic groups are present, converting into a physiologically tolerated salt.

* * * * *